United States Patent [19]

Westrup

[11] Patent Number: 4,539,181

[45] Date of Patent: Sep. 3, 1985

[54] GAS MONITOR HAVING AN INDICATOR BAND AND A FORETUBE

[75] Inventor: Bernhard Westrup, Lübeck, Fed. Rep. of Germany

[73] Assignee: Drägerwerk Aktiengesellschaft, Fed. Rep. of Germany

[21] Appl. No.: 542,212

[22] Filed: Oct. 14, 1983

[30] Foreign Application Priority Data

Nov. 16, 1982 [DE] Fed. Rep. of Germany ....... 3242304

[51] Int. Cl.³ ..................... G01N 21/01; G01N 31/22
[52] U.S. Cl. ........................................ 422/59; 422/86; 422/55; 422/61
[58] Field of Search .................. 422/59, 60, 86, 83, 422/93, 99, 102

[56] References Cited

U.S. PATENT DOCUMENTS

| | | | |
|---|---|---|---|
| 2,004,611 | 6/1935 | Kleinfelder | 422/83 |
| 3,033,655 | 5/1962 | Grosskopf | 422/86 |
| 3,388,975 | 6/1968 | Wallace | 422/59 |
| 3,503,711 | 3/1970 | Skala | 422/83 |
| 4,052,162 | 10/1977 | Clarke | 422/81 |

*Primary Examiner*—Michael S. Marcus
*Assistant Examiner*—Carol M. Delahunty
*Attorney, Agent, or Firm*—McGlew and Tuttle

[57] ABSTRACT

A gas monitor for measuring a test gas equipped with an indicator band comprises a foretube for chemically converting a gas to be measured contained in the test gas, the foretube comprising a glass tube having a tip at each end to be broken away for the passage of the gas therethrough and including a conversion effecting filling in the glass tube and a capillary tube defining a conduit parallel to the filling. In a gas monitor, an indicator band impregnated with an agent reacting with the special gas to be measured and contained in the tested gas, is moved to be exposed to a gas sample. For some gases, for example vinyl chloride, no chemically reacting indicators are known. In such instances, the sample to be tested is first directed through a foretube where the gas to be measured is converted to obtain a gas reacting with the indicator and thus measurable. In the inventive foretube, aside from the filling effecting the conversion, a capillary tube is mounted forming a parallel conduit. One stream of the gas sample then flows through the converting filling, and another stream flows through the capillary tube. The sample arrives at the indicator in its full amount as in prior art arrangements, yet the conversion in the foretube is substantially more effective and thus the determination is more reliable.

3 Claims, 1 Drawing Figure

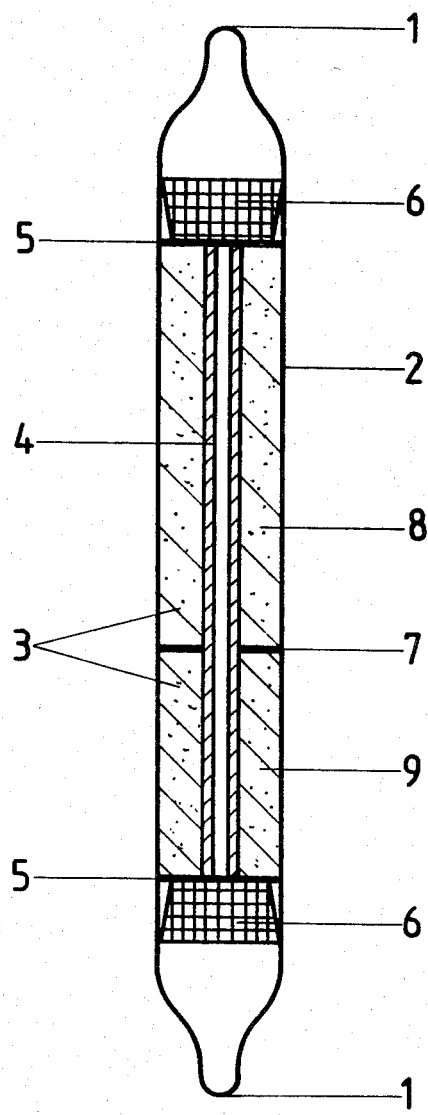

GAS MONITOR HAVING AN INDICATOR BAND AND A FORETUBE

FIELD AND BACKGROUND OF THE INVENTION

This invention relates in general to gas testing devices and in particular to a gas monitor with an indicator band and a foretube.

In prior art gas monitors, indicator bands are provided which are continuously or stepwise moved to be brought into contact with the gas to be monitored. The gas sample is fed in by a pump. Some of the gases to be measured cannot be determined with the indicator band directly. They do not react with the impregnating agent. Gases of this kind, for example vinyl chloride, must be chemically converted before they can be measured. The product thereby obtained, such as chlorine in this example, then reacts on the indicator band. The conversion takes place in a foretube, which is designed as a kind of a conventional gas detector tube. Within the gas monitor, such a foretube is disposed in the path of the sample upstream of the indicator band. The substance effecting the chemical conversion and received in the foretube determines the reaction time and thus the service time of the indicator band.

In a prior art device for monitoring fluids, an indicator band is mechanically advanced to bring it into contact with the fluid to be tested. A pump forces the fluid through the indicator band. The band indicates the noxious compounds of the fluid by changing color. However, no indicator is known for vinyl chloride. That is why a preliminary treatment of the fluid is necessary. To this end, a tube for preliminary treatment, or foretube, is provided upstream of the fluid inlet of the monitor, which is filled with a known oxidizing agent. While passing therethrough, vinyl chloride is oxidized to chlorine and indicators for chlorine are known (German OS No. 26 15 375). If a continuous monitoring is involved, the problem arises that even though the advance of the indicator band makes sure that always a fresh indicating portion is available for the test, the oxidizing agent in the foretube has only a limited capacity. This either undesirably reduces the service time, or requires larger sizes of foretubes with the result of unhandy dimensions and of an increased resistance to flow.

SUMMARY OF THE INVENTION

The present invention is directed to a test device with a foretube permitting monitoring for extended periods of time and also the measuring of gases which cannot be directly measured with the indicator band.

The invention includes a testing device in the form of a glass tube which has ends which are broken away for the passages of gas therethrough. In accordance with the invention wire mesh is arranged adjacent each end of the glass tube along with glass quilts for containing a decomposition layer which advantageously oxidizes a constituent such as vinyl chloride to deliver a free chlorine. This layer is referred to as a conversion-effecting filling which conditions the test gas so that the gas will provide an indication of its characteristics on an indicator band. In addition in accordance with the invention a capillary tube is arranged between the glass quilts and advantageously oriented centrally of the conversion-effecting filling. The capillary tube also permits the passage of test gas therethrough.

The surprising advantage obtained with the invention is a substantially extended useful life of the foretube, and thus service time of the gas monitor. Inventive foretubes can be inserted upstream of the monitor proper without any particular changes in the gas sample amounts to be delivered.

The gas sample directed against the measuring area of the indicator band passes through both the capillary tube and the conversion-effecting filling in the foretube in parallel streams and at the usual speed, so that the total flow gas to the indicator band is not changed, while in the foretube, conditions are obtained in the filling, which are more favorable to the portion of the gas sample which flows therethrough. In a specific embodiment, the parallel conduit may be formed by a capillary tube bypassing the foretube at the outside. The conditions are favorable since, despite the presence of the capillary tube, the area of the filling is still quite large but is exposed to less gas for conversion.

Accordingly, it is an object of the invention to provide an improved device for testing gases which includes a foretube containing a chemically converting material for a portion of the test gas as well as a capillary tube providing a conduit parallel to the filling.

A further object of the invention is to provide a gas testing device which is simple in design, rugged in construction and economical to manufacture.

The various features of novelty which characterize the invention are pointed out with particularity in the claims annexed to and forming a part of this disclosure. For a better understanding of the invention, its operating advantages and specific object attained by its uses, reference is made to the accompanying drawing and descriptive matter in which a preferred embodiment of the invention is illustrated.

BRIEF DESCRIPTION OF THE DRAWINGS

The only FIGURE of the drawings is a schematic sectional view of a testing tube constructed in accordance with the invention.

DESCRIPTION OF THE PREFERRED EMBODIMENT

Referring to the drawing in particular the invention embodied therein comprises a gas monitor for measuring a test gas which is equipped with an indicator band. The monitor comprises a foretube or glass tube 2 which is closed at both ends but which has breakaway tips 1, 1 at each end which when broken away will provide for a passage of the gas to be tested therethrough.

The foretube comprises a glass tube 2 which is closed at both ends where it terminates in break-away tips 1, and is filled with a conversion effecting substance 3 and accommodates a capillary tube 4 forming a parallel conduit. Capillary tube 4 is held in position between wire mesh bodies 6 through glass quilts 5. A porous disc 7 separates two parts of conversion-effecting filling 3 in glass tube 2 and has an aperture for holding tube 4.

Conversion-effecting filling 3, for example for converting vinyl chloride contained in the gas sample, includes a dry layer 8 and a decomposition layer 9 for oxidizing the vinyl chloride and thus splitting off free chlorine.

The fuel amount of the gas sample is directed through the foretube and flows in two separate streams, namely through the conversion-effecting filling 3 and through a capillary tube 4. The indicator band is thus exposed to the full amount of the gas sample. A lesser stream of the gas sample flows through the conversion-effecting filling 3 than through tube 4, so that substantially more favorable conditions for the conversion are created. The cross-sectional portion occupied by capillary tube 4 and thus the reduction of the cross-sectional area of flow in the filling is only small, however. The area of the conversion-effecting filling thus remains rather large. Since it receives less of the gas for conversion, it remains effective longer.

While a specific embodiment of the invention has been shown an described in detail to illustrate the application of the principles of the invention, it will be understood that the invention may be embodied otherwise without departing from such principles.

What is claimed:

1. A foretube for chemically converting a gas to be measured in a test gas which is adapted to flow through a monitor having an indicator band, comprising a glass tube having a breakaway tip at each end, a conversion-effecting filling in said glass tube and a capillary tube centrally arranged in said filling and defining a longitudinally extending open conduit which is parallel to said gas tube.

2. A foretube according to claim 1, including a wire-meshed body arranged at each end of said glass tube, and a glass quilt member disposed between each wire-meshed body and said capillary tube at each end of said capillary tube for holding said capillary tube in position.

3. A foretube according to claim 1, including a porous separating disc having an aperture therethrough and disposed in said conversion-effecting filling intermediate ends of said glass tube, said capillary tube extending through said disc aperture.

* * * * *